United States Patent [19]

Levine et al.

[11] Patent Number: 4,601,203

[45] Date of Patent: Jul. 22, 1986

[54] OXYGEN CONTENT SAMPLING SYSTEM

[75] Inventors: Robert A. Levine; Danny F. Davis, both of Westminster; Anthony W. Cordeiro, Huntington Beach, all of Calif.

[73] Assignee: Atlantic Richfield Company, Los Angeles, Calif.

[21] Appl. No.: 751,242

[22] Filed: Jul. 1, 1985

[51] Int. Cl.⁴ ............................................ G01N 27/00
[52] U.S. Cl. ................................. 73/432 R; 73/27 R
[58] Field of Search ..................... 73/432 R, 27 R, 25, 73/26, 321, 23, 24, 27 A

[56] References Cited

FOREIGN PATENT DOCUMENTS 586498 1/1925 France ................................. 73/321
30057 2/1984 Japan .................................... 73/23

Primary Examiner—Jerry W. Myracle
Attorney, Agent, or Firm—Frank J. Uxa

[57] ABSTRACT

An oxygen content sampling system is disclosed. The system includes an oxygen probe and monitor. The oxygen probe and interconnecting cable pass through a housing adapted to receive and protect the probe during periods of non-use.

4 Claims, 3 Drawing Figures

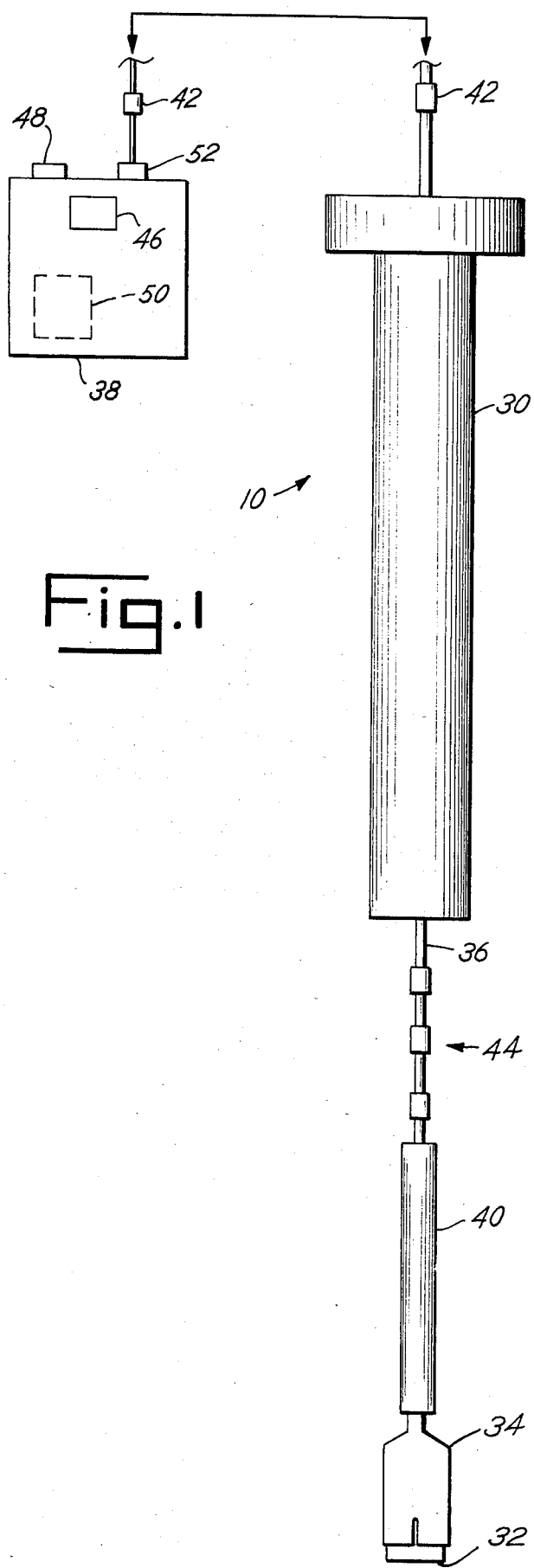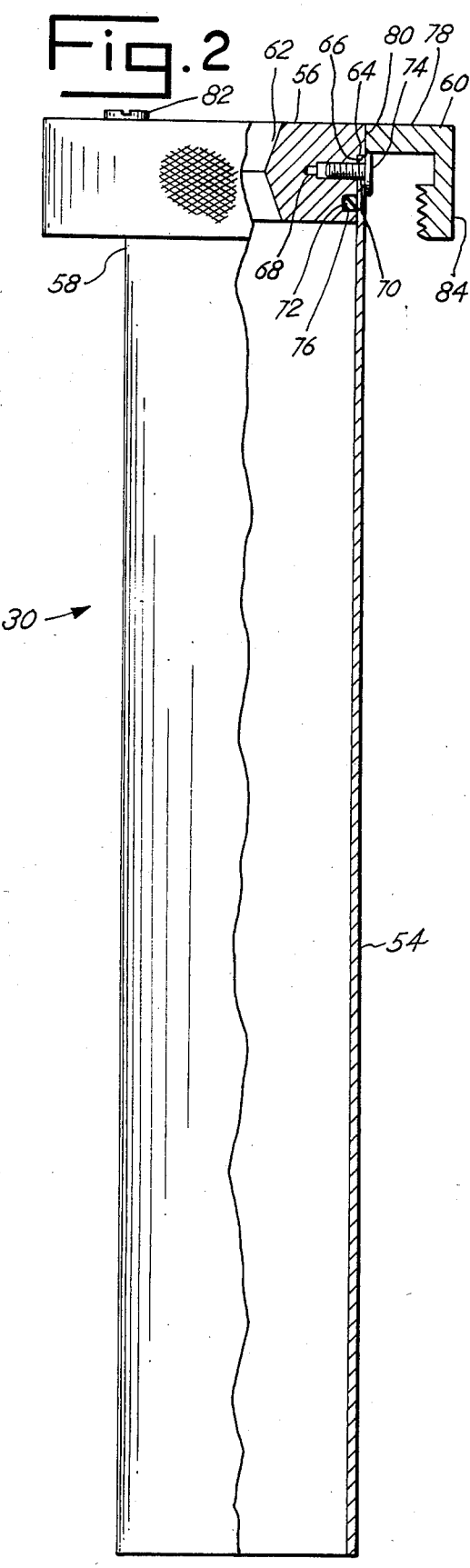

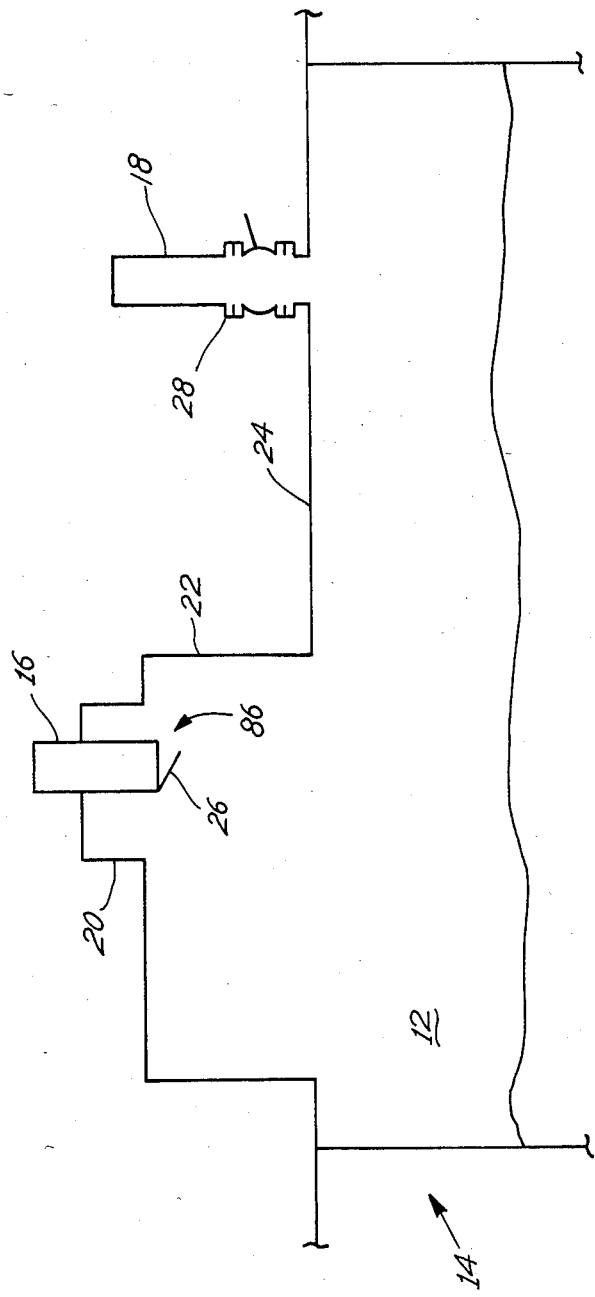

OXYGEN CONTENT SAMPLING SYSTEM

BACKGROUND OF THE INVENTION

The present invention relates generally to an oxygen content sampling system and more particularly to a sampling system for use in tank vessels of the type for transporting crude oil.

In the early 1970's, inert gas systems ("IGS") became the standard means of protection against explosions and fires in large, crude oil tank vessels. (As used herein, the term "inert" means non-combustible.) An inert gas, such as the stack gas from the tanker boiler, is pumped into the tank, purging combustible oxygen therefrom, and thereby substantially reducing the risk of explosion and/or fire.

Shortly thereafter, an antipollution measure, i.e., crude oil washing ("COW"), was soon developed. Crude oil washing utilizes high pressure jets, pumping crude oil, to wash the tank walls and thereby reduce clingage. Thus, the amount of combustible crude oil left on board after unloading is reduced.

Both IGS and COW are now required on crude carriers as a safety and antipollution measures, respectively. These requirements derive from the International Conference on Marine Pollution (1973) and the International Conference on Tanker Safety and Pollution Prevention (1978), often referred to collectively as MARPOL 73/78. Regulations promulgated thereunder are found in the Code of Federal Register, Title 33, Part 157.

To assure vessel safety during crude oil washing, Section 157.164, *USE OF INERT GAS SYSTEM*, provides, in pertinent part:

"(a) The master of a tank vessel . . . having a COW system . . . shall ensure the following:
  (1) Before each cargo tank is crude oil washed, the oxygen content in the tank is measured at each of the following locations in the tank:
    (i) One meter from the deck
    (ii) In the center of the ullage space."

The oxygen content must be at or below eight percent (8%) of volume to permit crude oil washing.

SUMMARY OF THE INVENTION

The present invention is an oxygen content sampling system for interconnection with the ullage and standpipe fittings on a tanker. The oxygen content sampling system is capable of accurately sensing the oxygen content at various positions and depths within the cargo tanks.

The system includes a housing, an oxygen probe, an oxygen monitor, and a weighted cable interconnecting the oxygen probe and monitor. The probe is positioned through the ullage or standpipe fitting and lowered to the appropriate depth, as shown by a series of length markings on the weighted cable.

The probe delivers an oxygen content signal, received by the oxygen monitor. The monitor responsively provides an alert, preferably both visible and audible, whenever the oxygen content at the oxygen probe exceeds a predetermined threshold.

The housing includes a substantially cylindrical, elongated sleeve, a collar defining a passageway, and a threaded cap. The weighted cable extends through the passageway, such that the oxygen probe can be protectively stored in the elongated sleeve during periods of non-use. The threaded cap is adapted to interconnect with the ullage or standpipe fitting.

It is thus an object of the present invention to provide an improved, accurate oxygen content sampling system. Another object is an improved oxygen sampling system for use on crude oil tankers.

It is another object to provide an oxygen monitoring system for use in the oil industry whereby the oxygen level can be accurately sensed at various positions and depths within a crude oil tanker. Still another object is a readily maintained oxygen content sampling system wherein the components are quickly and easily changed.

It is also an object of the present invention to provide a low-cost system utilizing conventional off-the-shelf components in conjunction with inexpensive, readily manufactured components. Yet another object is an oxygen content sampling system wherein the oxygen probe can be contained and protected.

These and other features, objects, and advantages of the present invention are set forth or implicit in the following detailed description.

BRIEF DESCRIPTION OF THE DRAWING

A preferred embodiment of the present invention is described, in detail, with reference to the drawing wherein:

FIG. 1 is a schematic diagram of the oxygen content sampling system;

FIG. 2 is a partial cross-sectional view of the housing shown in FIG. 1; and

FIG. 3 is a schematic diagram of a tanker.

DETAILED DESCRIPTION OF A PREFERRED EMBODIMENT

A preferred embodiment of the present invention is shown in FIGS. 1-2 as an oxygen content sampling system 10. Referring also to FIG. 3, the system 10 is used to sample the oxygen content or level in the tanks 12 of a crude oil vessel 14 through either a conventional ullage fitting 16 or standpipe fitting 18. As shown, the ullage fitting 16 is conventionally located upon an ullage cap 20 of a cargo tank hatch 22. The standpipe fitting 18 is conventionally located upon the deck 24 of the vessel 14. The ullage fitting 16 includes a conventional, spring-loaded check valve, shown schematically at 26; the standpipe fitting 18 includes a conventional, hand-operated ball valve, shown schematically at 28.

The oxygen content sampling system 10 includes a housing 30, an oxygen probe 32 plug compatible with a receptacle 34, a weighted cable 36 connected to the receptacle 34, and an oxygen monitor 38. The oxygen probe and receptacle 32, 34, cable 36 (unweighted) and monitor 38 are commercially available through GasTech, Inc., 331 Fairchild Drive, Mountain View, Calif. 94043. In this preferred embodiment, the three components comprise the GasTech Model OX-82 oxygen indicator. The probe 32 is preferably a $CO_2$ resistance cell type.

The cable 36 is weighted by addition of a lead band 40 adjacent the receptacle 34. Further, a series of brightly-colored bands or length markings 42 is attached to the cable 36 at five feet intervals to facilitate positioning the probe 32 at the proper depth within the tank 12. Finally, three bands 44 are secured to the cable 36 adjacent the lead band 40 at approximately six inch spacing.

The oxygen probe 32 senses the oxygen content or level in the immediate surrounding region of the tank 12 and issues an oxygen content signal, i.e., a voltage, representative and/or proportional thereto. The monitor 38 receives the oxygen content signal and responsively provides an oxygen content reading on a gauge 46.

The oxygen monitor 38 senses a rising oxygen content and provides an alert whenever a predetermined threshold is exceeded. Preferably, and in accordance with MARPOL 73/78, the threshold is eight percent oxygen by volume. In this preferred embodiment, the oxygen monitor 38 includes a visible alert in the form of a flashing red lamp 48 and an audible alert in the form of a buzzer 50. As shown, the cable 36 connects directly to the oxygen receptacle 34 and indirectly to the oxygen monitor 38 through a socket/receptacle arrangement 52.

Referring to FIG. 2, the housing 30 includes a substantially cylindrical, elongated sleeve 54, a collar 56 secured at one end 58 of the sleeve 54, and a threaded cap 60. The collar 56 defines a central, hourglass-shaped passageway 62 therethrough and circumferential offset surface 64 adapted to engage one edge 66 of the substantially cylindrical, elongated sleeve 54. The collar 56 further includes a series of equally-spaced screw holes 68, adapted to align with a series of screw openings 70 in the end 58 of the sleeve 54, and a circumferentially-extending groove 72.

The collar 56 is secured to the sleeve 54 by abutting the circumferential offset surface 64 against the edge 66 and driving screws 74 through the screw openings 70 into the screw holes 68. An O-ring 76 fits within the groove 72 to substantially seal the engagement between the sleeve 54 and collar 56.

The collar 56 and O-ring 76 are preferably split into substantially identical halves prior to assembly. This facilitates repair of the oxygen content sampling system 10 or, more particularly, replacement of the oxygen receptacle 34 and cable 36, which are integrally manufactured.

The threaded cap 60 is substantially annular, including a flange 78 adapted to frictionally engage and fit upon an upper portion 80 of the collar 56. A second series of screws 82 secures the flange 78 to the collar 56. The threaded cap 60 extends beyond the substantially cylindrical, elongated sleeve 54 and includes an internally-threaded arm 84 extending substantially perpendicular to the flange 78 along the sleeve 54. The arm 84 is adapted for interconnection to the ullage and standpipe fittings 16, 18 and has a knurled external surface to facilitate tightening.

When used with the ullage fitting 16, the elongated sleeve 54 actuates and opens the spring-loaded check valve 26. This, in turn, provides an access passage, generally designated 86 in FIG. 3, for the oxygen probe and receptacle 32, 34 and the weighted cable 36 through the check valve 26 and into the tank 12.

Referring again to FIGS. 1 and 2, the cable 36 and length markings 42 pass closely through the central passageway 62 of the collar 56. During sampling, an adequate seal between the cable 36 and collar 56 is achieved by application of a putty-like material or rag (not shown).

The oxygen probe and receptacle 32, 34 fit totally and snuggly within the elongated sleeve 54, such that the relatively fragile probe 32 is contained and protected during periods of non-use. Passage of the three closely-spaced bands 44, adjacent to lead band 40, through the collar 56 establishes that the probe 32 is fully situated within the sleeve 54.

The oxygen content sampling system 10 provides quick and accurate oxygen measurements within the tank 12. The system 10 further avoids the problems affiliated with stratified oxygen layers and the difficulties encountered with a measurement technique wherein atmospheric samples are withdrawn from the tank 12 for analysis. With respect to stratification, the probe 32 can be readily moved upwardly and downwardly whenever the potential for stratification is sensed.

The withdrawal-type system is the "Hermetic Oxy" system manufactured by TankSystem A.S. of Norway. The system includes a brass plug fitted onto a rubber hose, which is lowered into the tank through a deck-mounted valve. Gas samples are drawn through the hose to an oxygen analyzer outside the tank 12.

The difficulties with this type of system all relate to inaccurate oxygen content measurements. The reasons for inaccuracy are multiple. There may be leakage through the hose and/or fittings; the hose may twist or sway during testing altering the depth of the hose end; and purging of the hose prior to measurement may be incomplete. Furthermore, the sampling must be volumetrically controlled, which is difficult when the tank 12 is pressurized as is normally the case. These problems are substantially avoided by the present invention wherein sampling occurs within the tank 12 at the oxygen probe 32 utilizing non-pressure sensitive means.

The process for oxygen content measurement utilizing the sampling system 10 is as follows. The housing 30 is applied to the ullage or standpipe fitting 16, 18 by screwing the threaded cap 60 thereon. This provides the access passage 86 into the tank 12. The oxygen probe 32 is lowered, utilizing the length markings 42, to the appropriate depth through the collar 56 and the passageway 62 is sealed to the extent possible. The system 10 is then activated and oxygen content measurements made. If the oxygen content exceeds the predetermined threshold, then more inert gas is pumped into the tank 12 until a proper oxygen content is achieved.

A single preferred embodiment of the present invention has been described. It is to be understood, however, that certain changes and modifications can be made without departing from the true scope and spirit of the present invention, as defined by the following claims.

What is claimed is:

1. An oxygen content sampling system comprising, in combination:
   a housing including a substantially cylindrical, elongated sleeve, a collar secured at one end of said substantially cylindrical, elongated sleeve and defining a passageway therethrough, and a threaded cap secured to said collar and extending beyond said substantially cylindrical, elongated sleeve;
   an oxygen probe for sensing an oxygen content and issuing an oxygen content signal;
   a weighted cable extending from said oxygen probe through said passageway in said collar for transmission of said oxygen content signal, said weighted cable including thereon a series of length markings; and
   an oxygen monitor interconnected to said weighted cable for receipt of said oxygen content signal, said oxygen monitor issuing an alert whenever said oxygen content at said oxygen probe exceeds a predetermined threshold;

said substantially cylindrical, elongated sleeve being adapted to receive, contain, and protect said oxygen probe during periods of non-use.

2. An oxygen content sampling system as claimed in claim 1 wherein said predetermined threshold is eight percent oxygen by volume.

3. An oxygen content sampling system as claimed in claim 1 wherein said housing is adapted to connect with an ullage fitting of the type including a check valve, said substantially cylindrical, elongated sleeve being adapted to engage and open said check valve, thereby providing an access passage for said oxygen probe and said weighted cable.

4. An oxygen content sampling system as claimed in claim 1 wherein said collar includes two substantially identical halves to facilitate assembly and repair.

* * * * *